United States Patent [19]

Alpern et al.

[11] Patent Number: 4,482,053
[45] Date of Patent: Nov. 13, 1984

[54] SEALABLE CONTAINER FOR PACKAGING MEDICAL ARTICLES IN STERILE CONDITION

[75] Inventors: Marvin Alpern; Thomas F. Genova, both of Edison, N.J.

[73] Assignee: Ethicon, Inc., Somerville, N.J.

[21] Appl. No.: 552,511

[22] Filed: Nov. 16, 1983

[51] Int. Cl.³ .................... A61B 17/06; A61B 19/02
[52] U.S. Cl. ............................ 206/439; 206/484.1; 206/484; 220/359
[58] Field of Search .............. 206/484, 484.1, 484.2, 206/524.9, 439; 220/359, 360

[56] References Cited

U.S. PATENT DOCUMENTS

| | | | |
|---|---|---|---|
| 3,229,813 | 1/1966 | Crowe, Jr. et al. | 206/439 |
| 3,819,106 | 6/1974 | Schuster | 206/439 |
| 4,057,144 | 11/1977 | Schuster | 206/439 |
| 4,176,746 | 12/1979 | Kooi | 206/484.1 |
| 4,203,520 | 5/1980 | Schuster | 206/439 |
| 4,367,816 | 1/1983 | Wilkes | 206/484.1 |

FOREIGN PATENT DOCUMENTS 2025894 1/1980 United Kingdom ............... 206/439

Primary Examiner—Joseph Man-Fu Moy
Attorney, Agent, or Firm—Charles J. Metz

[57] ABSTRACT

There is described a double sterile package for packaging medical articles in a sterile condition which can be sterilized in one ethylene oxide sterilization cycle. The package comprises:

(a) a sealable inner package formed of impervious sheet material, said inner package being arranged and constructed to contain said medical product, wherein the inner package has a heat sealable vent at a predetermined location thereon; and (b) a sealable outer package formed of sheet material that is impervious to bacteria, at least a portion of the outer package being formed of sheet material that is pervious to sterilizing gas, the outer package being arranged and constructed to receive said inner package therein and to snugly hold the inner package in a predetermined position, wherein the outer package contains means positioned to be adjacent said vent when the inner package is contained in the outer package in said predetermined position, said means being capable of transmitting sufficient heat therethrough to heat seal said vent without said means itself being heat sealed to said inner package.

6 Claims, 5 Drawing Figures

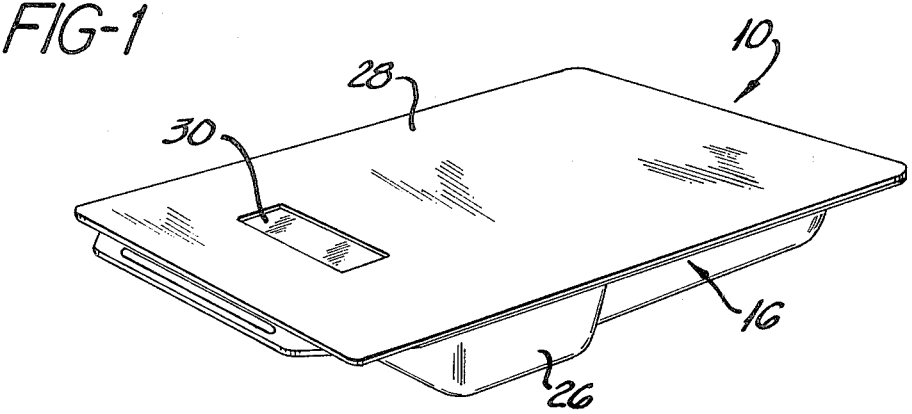
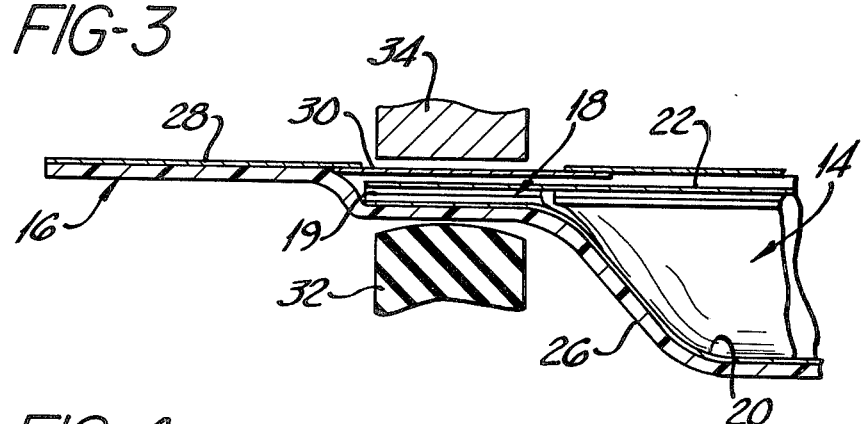
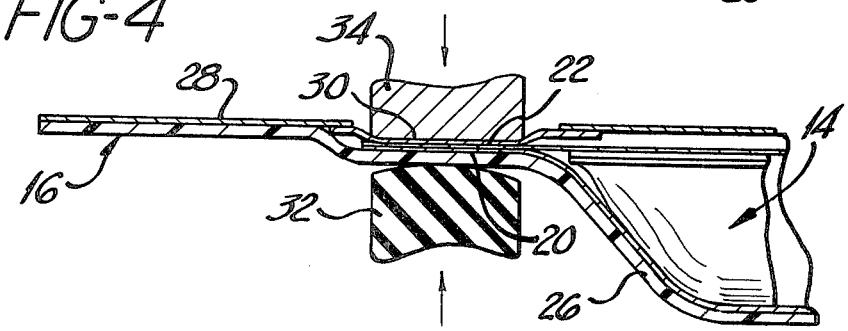

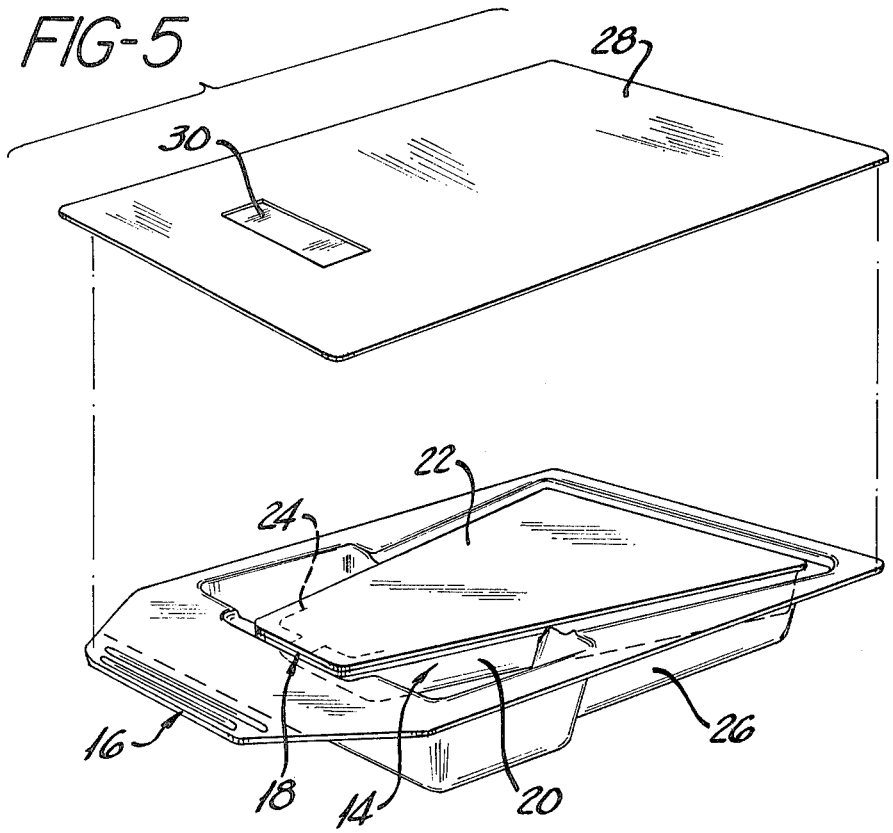

SEALABLE CONTAINER FOR PACKAGING MEDICAL ARTICLES IN STERILE CONDITION

The invention relates to a sealable package for packaging medical articles in a sterile condition, and is particularly adapted for packaging articles for ethylene oxide sterilization.

BACKGROUND OF THE INVENTION

One type of packaging for sterile medical devices uses a double sterile package having a sealed primary package that contains the device and a secondary sealed package. The primary package is contained inside the secondary package, with the contents of both packages being in a sterile condition. Certain types of materials from which medical devices are made must be sterilized by ethylene oxide, because the preferred mode of sterilizing via gamma radiation causes excessive degradation of such materials. Polypropylene and synthetic absorbable polymers such as polyglycolic acid and poly-(p-dioxanone) are illustrative of such materials that undergo an undesirable degree of degradation upon exposure to a sufficient dose of gamma radiation to effect sterilization.

A typical package of this type adapted for ethylene oxide sterilization employs a sealed metal foil pack as the primary package, and as the secondary package a relatively rigid tray having a cover of a material that is impervious to bacteria but which is pervious to ethylene oxide gas. Spunbonded polyethylene (such as duPont's TYVEK) is illustrative of such materials. The sterilization procedure used with such a package would ordinarily employ two cycles. Initially, the foil pack containing the medical device to be sterilized is partially sealed, is then sterilized with ethylene oxide gas, and the seal is completed in a sterile atmosphere. The foil pack is then sealed in the secondary package containing an ethylene oxide-pervious cover, and the package as a whole is then subjected to a second ethylene oxide sterilization step.

This invention provides a double sterile package that can be sterilized by ethylene oxide gas in one sterilization cycle.

BRIEF SUMMARY OF THE INVENTION

The invention provides a package for encasing a sterile medical product, which comprises:

(a) a sealable inner package formed of impervious sheet material, said inner package being arranged and constructed to contain said medical product, wherein the inner package has a heat sealable vent at a predetermined location thereon; and (b) a sealable outer package formed of sheet material that is impervious to bacteria, at least a portion of the outer package being formed of sheet material that is pervious to sterilizing gas, the outer package being arranged and constructed to receive said inner package therein and to snugly hold the inner package in a predetermined position, wherein the outer package contains means positioned to be adjacent said vent when the inner package is contained in the outer package in said predetermined position, said means being capable of transmitting sufficient heat therethrough to heat seal said vent without said means itself being heat sealed to said inner package.

THE PRIOR ART

Komatsu et al., U.S. Pat. No. 3,892,058, disclose a process for sterilizing a container composed of a metal foil layer and a heat sealable resin film.

Daly et al., U.S. Pat. No. 4,177,620, disclose a method for sterilizing a package which has a plastic member heat sealed around three sides to a paper member.

Schuster, U.S. Pat. No. 4,022,324, discloses a sealed container which is sterilized after an article has been placed therein. The container comprises a bottom tray portion, a flexible cover portion including a bacteria-impermeable panel means and a passage means, and a bacteria-impermeable, sterilizing vapor-permeable membrane.

Kemble, U.S. Pat. No. 3,613,879, is an illustration of a conventional suture package having an inner and an outer envelope which is sterilized by ethylene oxide.

BRIEF DESCRIPTION OF THE DRAWINGS

FIG. 1 is a perspective view of a package embodying the principles of the invention;

FIG. 3 is a cross-sectional side view of a portion of the package of FIG. 1 showing the vent before it is sealed;

FIG. 4 is a view similar to FIG. 3 showing the vent sealed; and

FIG. 5 is a perspective view of the package of FIG. 1 with the cover sheet removed.

DETAILED DESCRIPTION OF THE INVENTION

Figure 2:
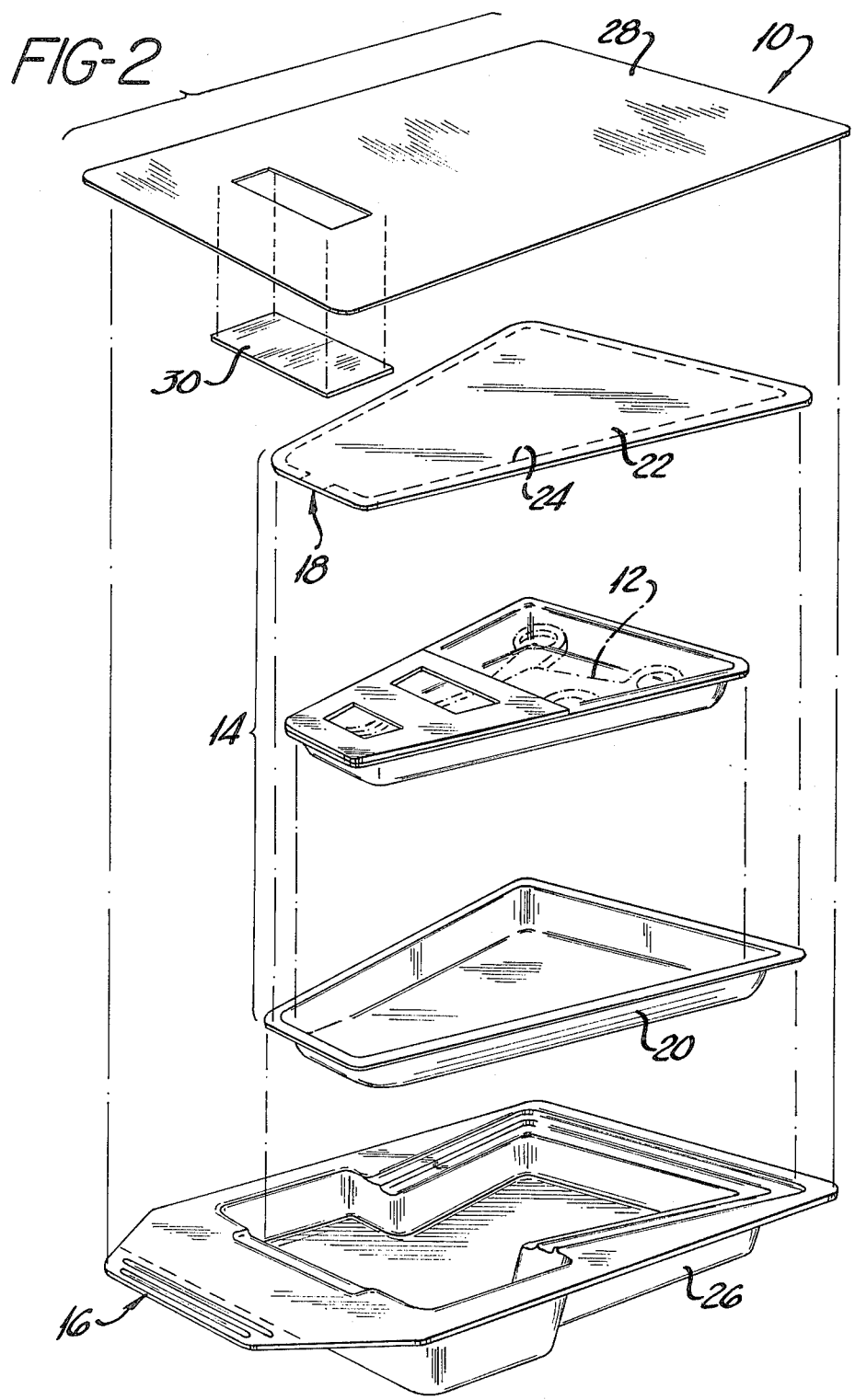
FIG. 2 is an exploded perspective view of the package of FIG. 1.

Referring now to the drawings, in FIGS. 1 and 2, there is shown a package 10 for a sterile medical product such as a multiple clip applier for applying absorbable ligating clips made of a polymeric material such as polydioxanone that cannot be sterilized by gamma radiation, but which must be sterilized by a sterilizing gas such as ethylene oxide. The multiple clip applier is shown in phantom in FIG. 2 as 12. The package 10 is composed of an inner package 14 and an outer package 16. The inner package 14 is made of a material such as metal foil that is completely sealed except for a vent 18 at one end thereof. Conveniently, the inner package 14 is composed of a shaped bottom portion 20 and a relatively flat cover sheet 22. The cover sheet 22 is sealed to the shaped bottom portion 20 completely around the edge 24, except at the vent 18. However, there is a layer of heat sealable material applied to either the cover sheet 22 and/or the shaped bottom portion 20 in the area of the vent 18 so that the vent 18 can be heat sealed at an appropriate time in the sterilization cycle.

The outer package 16 is composed of a fairly rigid tray 26 composed of a thermoformable material such as high density polyethylene. The tray 26 is shaped so as to receive the inner package 14 and hold it snugly in a predetermined position, as is shown in the drawings (e.g., FIG. 5). The outer package 16 also includes a sterilizing gas-pervious cover sheet 28, which is impervious to bacteria, such as spun bonded polyethylene (for instance Dupont's TYVEK).

The gas pervious cover sheet 28 contains a metal foil "window" 30 which is located such that when the inner package 14 is placed in the tray 26, and the gas pervious cover sheet 28 is sealed onto the tray 26, the metal foil window 30 will be positioned just over the vent 18 (see FIGS. 3 and 4). Therefore, when the package 10 is being employed to contain a medical article such as the multiple clip applier 12 shown in the drawings, the applier 12 is first sealed into the inner package 14, leaving only the vent 18 unsealed, the inner package 14 is placed in the tray 26 in position as shown in FIG. 5, and then the gas pervious cover sheet 28 is heat sealed completely onto the top of the tray 26. The entire package 10 is then exposed to an atmosphere of ethylene oxide, which permeates through the gas pervious cover sheet 28 and into the interior of both the outer package 16 and through the vent 18 into the interior of the inner package 14 to thereby sterilize the medical device 12 contained therein. At the end of the ethylene oxide sterilization cycle, the sterilized package 10 is then removed to the atmosphere, which need not be sterile, and then the vent 18 is heat sealed by conventional means such as is shown in FIGS. 3 and 4 wherein the package 10 is positioned such that the portion just under the vent 18 is placed on a rubber sealing base 32 and a hot sealing dye 34 is applied to the metal foil window 30 to have the heat transmitted through the metal foil window 30 and to heat seal the vent 18.

By following the principles of this invention, it is seen that one ethylene oxide sterilization cycle can be eliminated from the prior sterilization procedure that was discussed above in the Background of the Invention section of this application.

What is claimed is:

1. A package for encasing a sterile medical product, which comprises:

(a) a sealable inner package formed of impervious sheet material, said inner package being arranged and constructed to contain said medical product, wherein the inner package has a heat sealable vent at a predetermined location thereon; and (b) a sealable outer package formed of sheet material that is impervious to bacteria, at least a portion of the outer package being formed of sheet material that is pervious to sterilizing gas, the outer package being arranged and constructed to receive said inner package therein and to snugly hold the inner package in a predetermined position, wherein the outer package contains means positioned to be adjacent said vent when the inner package is contained in the outer package in said predetermined position, said means being capable of transmitting sufficient heat therethrough to heat seal said vent without said means itself being heat sealed to said inner package.

2. The package of claim 1 wherein said outer package is at least partially constructed of spun-bonded polyolefin.

3. The package of claim 2 wherein the spun-bonded polyolefin is spun-bonded polyethylene.

4. The package of claim 1 wherein said means comprises metal foil.

5. The package of claim 2 wherein said means comprises metal foil.

6. The package of claim 3 wherein said means comprises metal foil.

* * * * *